United States Patent [19]

Sugawara et al.

[11] Patent Number: 5,157,130
[45] Date of Patent: Oct. 20, 1992

[54] METHOD OF PREVENTING DISCOLORING OF MALEIC ANHYDRIDE

[75] Inventors: Harusige Sugawara; Takasi Ohkawa, both of Osaka, Japan

[73] Assignee: Mitsui Toatsu Chemicals, Incorporated, Tokyo, Japan

[21] Appl. No.: 499,430
[22] PCT Filed: May 23, 1990
[86] PCT No.: PCT/JP90/00656
 § 371 Date: Jun. 20, 1990
 § 102(e) Date: Jun. 20, 1990
[87] PCT Pub. No.: WO90/14345
 PCT Pub. Date: Nov. 29, 1990

[30] Foreign Application Priority Data

May 24, 1989 [JP] Japan .................................. 1-128626

[51] Int. Cl.$^5$ ............................................ C07D 307/60
[52] U.S. Cl. ................................... 549/203; 549/262
[58] Field of Search ................................. 549/203, 262

[56] References Cited

U.S. PATENT DOCUMENTS 2,296,218  9/1942  Middleton, Jr. ..................... 549/462
3,903,117  9/1975  Stenseth et al. .................... 549/203

FOREIGN PATENT DOCUMENTS 49-110624  10/1974  Japan .

Primary Examiner—Bernard Dentz
Attorney, Agent, or Firm—Burns, Doane, Swecker & Mathis

[57] ABSTRACT

A monochloro-substituted aliphatic alcohol containing 3–8 carbon atoms, a copper compound and a zinc compound are added to maleic anhydride to prevent discoloration of the maleic anhydride. Deterioration of the quality of the maleic anhydride can be inhibited when it is stored for a long period of time or heat-melted.

9 Claims, No Drawings

METHOD OF PREVENTING DISCOLORING OF MALEIC ANHYDRIDE

TECHNICAL FIELD

The present invention relates to a method of preventing maleic anhydride from discoloring and more particularly, to a method of improving its thermal stability and preventing discoloration of maleic anhydride when stored for a long period of time and heat-melted.

BACKGROUND ART

Maleic anhydride is a typical unsaturated dibasic acid obtainable by the catalytic oxidation of benzene or a fraction of hydrocarbons containing 4 carbon atoms (hereinafter referred to as the $C_4$ fraction). Maleic anhydride has two carboxyl groups in the form of acid anhydride and a highly reactive double bond. Therefore, various chemical reactions can be effected by using maleic anhydride.

Maleic anhydride is usually produced by catalytically oxidizing benzene or the $C_4$ fraction in a vapor phase and distilling the resulting reaction products.

However, the maleic anhydride thus obtained by distillation still contains trace amounts of impurities that are difficult to separate such as oxidation by-products and the like. Therefore, the thus-obtained maleic anhydride lacks thermal stability and has a tendency to become discolored when heat-melted. This tendency becomes marked when it is stored for a long period of time. This discoloration upon heat-melting exerts adverse effects on the quality of secondary products produced from maleic anhydride and remarkably impairs their commercial value.

It is therefore strictly required that maleic anhydride for industrial use be free from the discoloration phenomenon at the time of heat-melting and during storage for a long period of time.

In view of the above, various methods have been proposed for the prevention of the discoloration of maleic anhydride. The present inventors proposed a method for improving the thermal stability of maleic anhydride by adding n-propyl gallate, cuprous chloride and zinc chloride to maleic anhydride.

However, the prior methods are still insufficient to meet the severe requirements in quality of these days when maleic anhydride is stored in a solid state for a long period of time. Additives known in the prior art such as phenols and catechols have such a tendency that the additives per se become a cause for discoloring if used in large quantities.

In addition, phenols and catechols also have such disadvantages that they may be rendered ineffective with the lapse of time by external factors such as light, oxygen, and the like. Studies have therefore been made in search of excellent color stabilizers for maleic anhydride which can be free from such factors, in particular, discoloration at elevated temperatures.

The present inventors have conducted intensive studies on the above problems and found that the problems can be solved by using a monochloro-substituted aliphatic alcohol, a copper compound and a zinc compound in combination. Thus the present invention has been completed.

DISCLOSURE OF INVENTION

According to the present invention, there is provided a method of preventing discoloration of maleic anhydride which comprises adding to maleic anhydride a monochloro-substituted aliphatic alcohol containing 3–8 carbon atoms, a copper compound and a zinc compound.

Starting materials for producing maleic anhydride are benzene or the $C_4$ fraction which may be produced by decomposing, for example, naphtha. The $C_4$ fraction is mainly composed of n-butane (at least 96 % by weight) and the other components are isobutane, propane, pentane and the like.

Upon catalytically oxidizing benzene or the $C_4$ fraction, there is often used a catalyst of a vanadium-molybdenum system or a vanadium-phosphorus system. The catalytic oxidation is usually effected at 350°–550° C.

Reaction products produced by catalytic oxidation of benzene or the $C_4$ fraction are usually cooled to 70°–90° C. to obtain crude maleic anhydride. A part of the resulting maleic anhydride absorbs water so as to be converted to maleic acid. By dehydrating the maleic acid, there is produced again crude maleic anhydride, which is then distilled to obtain purified maleic anhydride. Distillation is usually effected at the bottom temperature of a distillation tower of 120°–160° C. under reduced pressure.

According to the method of the present invention, monochloro-substituted aliphatic alcohols having 3–8 carbon atoms are used. They are preferably monohydric or dihydric alcohols.

Exemplary suitable monochloro-substituted aliphatic alcohols having 3–8 carbon atoms include 1-chloro-2-propanol, 2-chloro-1-propanol, 3-chloro-1-propanol, 4-chloro-1-butanol, 5-chloro-1-pentanol, 6-chloro-1-hexanol, 7-chloro-1-heptanol, 8-chloro-1-octanol, 2-chloro-1,3-propanediol, 3-chloro-1,2-propanediol, 2-chloro-1-butanol, and the like. Among these alcohols, 4-chloro-1-butanol, 5-chloro-1-pentanol, 6-chloro-1-hexanol, 2-chloro-1,3-propanediol and 3-chloro-1,2-propanediol are particularly preferred.

Exemplary suitable copper compounds include organic or inorganic salts of copper, for example, copper halides such as copper (I) chloride, copper (II) chloride, copper (I) bromide, copper (II) bromide and the like, copper (I) sulfate, copper (II) sulfate, copper (I) nitrate, copper (II) nitrate, copper oxide, powder of metallic copper, copper (I) benzoate, copper (II) benzoate, copper (I) acetate, copper (II) acetate and the like. Among these copper compounds, copper (I) chloride, copper (II) chloride, copper (II) acetate and copper (II) benzoate are particularly preferred.

Exemplary suitable zinc compounds include organic or inorganic salts of zinc, for example, powder of metallic zinc, zinc oxide, zinc halides such as zinc chloride, zinc bromide and the like, zinc sulfate, zinc nitrate, zinc acetate, zinc benzoate, and the like. Zinc chloride and zinc acetate are particularly preferred.

It is already known that the above copper compounds and zinc compounds are effective stabilizers for maleic anhydride. However, they do not exhibit marked stabilization effects even when used in combination. According to the present invention, outstanding stabilization effects can be attained for a long period of time when a mono-chloro-substituted aliphatic alcohol containing 3 to 8 carbon atoms is used in combination with the two compounds.

In the practice of the present invention, there is no particular restriction on the method of incorporating the stabilizers into maleic anhydride. For example, the stabilizers may be added to purified maleic anhydride obtained by distillation or to purified maleic anhydride stored in the molten state, followed by the stirring thereof.

The three components may be added in any order. It is also possible to add a mixture of more than one of them. In any case, the desired effects can be attained with certainty.

The amounts of the stabilizers added are preferably 1 to 1000 ppm, more preferably 5 to 60 ppm for chlorine-substituted alcohols, preferably 0.1 to 5 ppm, more preferably 0.25 to 1 ppm for copper compounds, and preferably 0.05 to 5 ppm, more preferably 0.1 to 0.5 ppm for zinc compounds (the concentrations are based on the weight of maleic anhydride).

In order to enhance the effect of the present invention, for example, rectification distillation is carried out by adding tridecyl phosphite, a phosphorus type antioxidant, to maleic anhydride, or a phosphorus type antioxidant is added to maleic anhydride and a heat treatment is effected, for example, at 120°–190° C. for 1–10 hours and then the maleic anhydride is subjected to rectification distillation.

According to the present invention, not only can discoloration be prevented, but also the yield of maleic anhydride can be increased remarkably. That is, purified maleic anhydride can be obtained by rectification distillation of crude maleic anhydride, and heretofore, a distillate rate of a light boiling point fraction which could be cut has amounted to as high as 20-30 %, but according to the present invention, said distillate rate can be reduced to as low as 3-5 % to a great extent. That is, the rate of cut of the first fraction can be greatly lowered according to the present invention. More in detail, according to the present invention, even if maleic anhydride contains impurities causing discoloration of maleic anhydride, the discoloration can be suppressed, and therefore, a light boiling point fraction containing some impurities can be used as a product. As a result, the yield of maleic anhydride in rectification distillation can be improved.

In addition, the thermal stability of the thus-produced maleic anhydride is not impaired at all. Therefore, the economical effect is very large.

In summary, according to the present invention, discoloration of maleic anhydride during storage for a long period of time can be prevented with a very small amount of the additives which themselves do not deteriorate with time, and thereby deterioration of the quality of maleic anhydride is inhibited resulting in maintaining its high quality. The method of the present invention is excellent from an economical point of view.

In addition, the yield of maleic anhydride can be improved to a great extent and thereby, the method of the present invention is a highly economical method.

BEST MODE FOR CARRYING OUT THE INVENTION

The present invention will be further explained by the following examples and comparative examples. It should however be understood that the invention is by no means limited thereto.

In the examples, "ppm" is based on weight, and "molten color" indicates the APHA of the hue of maleic anhydride measured in a molten state in accordance with JIS (Japanese Industrial Standards) K-1359. "Heat-melted color" indicates the APHA of the hue of maleic anhydride which has been placed in a quartz test tube having a diameter of ca. 20 mm and a height of 150 mm (the same test tube used in the determination of molten color according to JIS K-1359) and heat-melted by dipping the test tube for 60 minutes in an oil bath maintained at a temperature of 181° C.

EXAMPLES 1-13

Into a four-necked glass flask was charged 1,000 g of crude maleic anhydride prepared by the catalytic oxidation (catalyst: divanadyl pyrophosphate, reaction temperature: 430° C.) of $C_4$ fraction (Composition: isobutane 0.8 wt %, n-butane 98.0 wt % and pentanes 1.2 wt %), and then tridecyl phosphite ("Mark 3010", tradename, manufactured by Adeca Argus Chemical Co., Ltd.) was added thereto up to a concentration of 200 ppm. The flask was fitted into a packed rectification tower (Packing: Dixon Packing ⅛ inch, size of packed portion: 20 mm in diameter × 1000 mm in height) followed by heat-treatment at 185° C. for 4 hr., and distillation was carried out under reduced pressure at a reflux ratio of 3 while maintaining the still temperature at 125° C.

To the purified maleic anhydride fraction at a distillation rate of 5-90 % were added a monochloro-substituted alcohol, a copper compound and zinc compound in the respective specified amounts, and they were uniformly dispersed and mixed, and the resulting mixture was allowed to stand for 60 min. while warming. Then the molten color and heat-melted color were determined respectively.

The samples were then allowed to stand in a solid state for 24 hours, 30 days or 60 days and then remelted to determine their molten color and heat-melted color. The results obtained are shown in Tables 1 and 2.

TABLE 1

| | Additives | Amount Added (ppm) | Immediately After Addition | | After 24 Hrs | | After 30 Days | | After 60 Days | |
|---|---|---|---|---|---|---|---|---|---|---|
| | Additives | | A | B | A | B | A | B | A | B |
| Control | — | — | 5 | 300 | 5 | 400 | 10 | >500 | 15 | >500 |
| Example 1 | 4-chloro-1-butanol | 10 | | | | | | | | |
| | Copper acetate | 1 | 5 | 15 | 5 | 20 | 5 | 40 | 10 | 60 |
| | Zinc acetate | 0.2 | | | | | | | | |
| Example 2 | 4-Chloro-1-butanol | 20 | | | | | | | | |
| | Cuprous chloride | 1 | 5 | 10 | 5 | 15 | 5 | 35 | 5 | 50 |
| | Zinc chloride | 0.2 | | | | | | | | |
| Example 3 | 4-Chloro-1-butanol | 20 | | | | | | | | |
| | Copper benzoate | 1 | 5 | 15 | 5 | 15 | 5 | 30 | 5 | 40 |
| | Zinc benzoate | 0.2 | | | | | | | | |
| Example 4 | 5-Chloro-1-pentanol | 20 | | | | | | | | |
| | Copper acetate | 1 | 5 | 10 | 5 | 15 | 5 | 35 | 5 | 50 |
| | Zinc acetate | 0.2 | | | | | | | | |

TABLE 1-continued

| | Additives | Amount Added (ppm) | Immediately After Addition A | B | After 24 Hrs A | B | After 30 Days A | B | After 60 Days A | B |
|---|---|---|---|---|---|---|---|---|---|---|
| Example 5 | 6-Chloro-1-hexanol | 10 | | | | | | | | |
| | Copper acetate | 1 | 5 | 15 | 5 | 25 | 5 | 40 | 5 | 60 |
| | Zinc acetate | 0.2 | | | | | | | | |
| Example 6 | 3-Chloro-1,2-pro-propanediol | 10 | | | | | | | | |
| | Copper acetate | 1 | 5 | 15 | 5 | 25 | 5 | 40 | 5 | 40 |
| | Zinc acetate | 0.2 | | | | | | | | |
| Example 7 | 3-Chloro-1,2-propanediol | 20 | | | | | | | | |
| | Copper acetate | 1 | 5 | 15 | 5 | 20 | 5 | 35 | 5 | 45 |
| | Zinc acetate | 0.2 | | | | | | | | |

[Notes]
A: Molten color (APHA)
B: Heat-melted color (APHA)

TABLE 2

| | Additives | Amount Added (ppm) | Immediately After Addition A | B | After 24 Hrs A | B | After 30 Days A | B | After 60 Days A | B |
|---|---|---|---|---|---|---|---|---|---|---|
| Example 8 | 3-Chloro-1,2-propane-diol | 5 | | | | | | | | |
| | Copper acetate | 1 | 5 | 20 | 5 | 40 | 5 | 60 | 10 | 70 |
| | Zinc acetate | 0.2 | | | | | | | | |
| Example 9 | 3-Chloro-1,2-propane-diol | 10 | | | | | | | | |
| | Cuprous chloride | 1 | 5 | 15 | 5 | 25 | 5 | 35 | 5 | 40 |
| | Zinc chloride | 0.2 | | | | | | | | |
| Example 10 | 3-Chloro-1,2-propane-diol | 60 | | | | | | | | |
| | Cuprous chloride | 1 | 5 | 10 | 5 | 15 | 5 | 20 | 5 | 30 |
| | Zinc chloride | 0.2 | | | | | | | | |
| Example 11 | 3-Chloro-1,2-propane-diol | 30 | | | | | | | | |
| | Cupric chloride | 1 | 5 | 15 | 5 | 20 | 5 | 25 | 5 | 35 |
| | Zinc chloride | 0.2 | | | | | | | | |
| Example 12 | 3-Chloro-1,2-propane-diol | 10 | | | | | | | | |
| | Copper benzoate | 1 | 5 | 15 | 5 | 20 | 5 | 40 | 5 | 60 |
| | Zinc benzoate | 0.2 | | | | | | | | |
| Example 13 | 3-Chloro-1,3-propane-diol | 20 | | | | | | | | |
| | Copper acetate | 1 | 5 | 15 | 5 | 20 | 5 | 30 | 5 | 40 |
| | Zinc acetate | 0.2 | | | | | | | | |

[Notes]
A: Molten color (APHA)
B: Heat-melted color (APHA)

EXAMPLES 14-15, COMPARATIVE EXAMPLES 1-2

Following the procedure of Examples 1-13, rectification was conducted except that the distillation rate was changed. To the thus-purified maleic anhydride was added a stabilizer, and the molten color and heat-melted color were determined. Further, in order to investigate the change with time the samples were then allowed to stand at a solid state for 24 hours, 30 days, 60 days and 90 days, and remelted to determine their molten color and heat-melted color. The results are shown in Table 3.

TABLE 3

| | Distillation rate in rectification (%) | Additives | Amount Added (ppm) | Immediately After Addition A | B | After 24 Hrs A | B | After 30 Days A | B | After 60 Days A | B | After 90 Days A | B |
|---|---|---|---|---|---|---|---|---|---|---|---|---|---|
| Example 14 | 3-90 | 3-Chloro-1,2-propanediol | 20 | 5 | 10 | 5 | 15 | 5 | 40 | 10 | 60 | 15 | 80 |
| | | Cuprous chloride | 1 | | | | | | | | | | |
| | | Zinc chloride | 0.2 | | | | | | | | | | |
| Example 15 | 20-90 | 3-Chloro-1,2-propanediol | 20 | 5 | 10 | 5 | 15 | 5 | 20 | 10 | 30 | 10 | 40 |
| | | Cuprous chloride | 1 | | | | | | | | | | |
| | | Zinc chloride | 0.2 | | | | | | | | | | |
| Comparative Example 1 | 3-90 | n-Propyl gallate | 2 | 5 | 30 | 5 | 60 | 15 | 100 | 25 | 200 | 30 | 300 |
| | | Cuprous chloride | 1 | | | | | | | | | | |
| | | Zinc chloride | 0.2 | | | | | | | | | | |
| Comparative Example 2 | 20-90 | n-Propyl gallate | 2 | 5 | 10 | 5 | 15 | 5 | 20 | 25 | 70 | 25 | 150 |
| | | Cuprous chloride | 1 | | | | | | | | | | |

TABLE 3-continued

| Distillation rate in rectification (%) | Additives | Amount Added (ppm) | Immediately After Addition | | After 24 Hrs | | After 30 Days | | After 60 Days | | After 90 Days | |
|---|---|---|---|---|---|---|---|---|---|---|---|---|
| | | | A | B | A | B | A | B | A | B | A | B |
| | Zinc chloride | 0.2 | | | | | | | | | | |

[Notes]
A: Molten color (APHA)
B: Heat-melted color (APHA)

INDUSTRIAL APPLICABILITY

Maleic anhydride is a valuable compound which can be widely used as a raw material for producing unsaturated polyester resins, fumaric acid, succinic acid, maleic acid, sizing agents for papers, stabilizers for polyvinyl chloride, plasticizers, agricultural chemicals, surface active agents, and the like.

According to the present invention, the resulting maleic anhydride has an improved thermal stability and its discoloration is prevented even when it is stored for a long period of time or heat-melted.

We claim:

1. A method of preventing discoloration of maleic anhydride which comprises adding to maleic anhydride a monochloro-substituted aliphatic alcohol containing 3-8 carbon atoms, a copper compound and a zinc compound.

2. The method according to claim 1 in which 1-1000 ppm by weight of the monochloro-substituted aliphatic alcohol containing 3-8 carbon atoms, 0.1-5 ppm by weight of the copper compound and 0.05-5 ppm by weight of the zinc compound based on the weight of maleic anhydride are added.

3. The method according to claim 1 in which 5-60 ppm by weight of the monochloro-substituted aliphatic alcohol containing 3-8 carbon atoms, 0.25-1 ppm by weight of the copper compound and 0.1-0.5 ppm by weight of the zinc compound based on the weight of maleic anhydride are added.

4. The method according to claim 1 in which the monochloro-substituted aliphatic alcohol containing 3-8 carbon atoms is a member selected from the group consisting of 1-chloro-2-propanol, 2-chloro-1-propanol, 3-chloro-1-propanol, 4-chloro-1-butanol, 5-chloro-1-pentanol, 6-chloro-1-hexanol, 7-chloro-1-heptanol, 8-chloro-1-octanol, 2-chloro-1,3-propanediol, 3-chloro-1,2-propanediol, and 2-chloro-1-butanol.

5. The method according to claim 1 in which the monochloro-substituted aliphatic alcohol containing 3-8 carbon atoms is selected from the group consisting 4-chloro-1-butanol, 5-chloro-1-pentanol, 6-chloro-1-hexanol, 2-chloro-1,3-propanediol, and 3-chloro-1,2-propanediol.

6. The method according to claim 1 in which the copper compound is selected from the group consisting of copper halides, copper (I) sulfate, copper (II) sulfate, copper (I) nitrate, copper (II) nitrate, copper oxide, powder of metallic copper, copper (I) benzoate, copper (II) benzoate, copper (I) acetate, and copper (II) acetate.

7. The method according to claim 1 in which the copper compound is a member selected from the group consisting of copper (I) chloride, copper (II) chloride, copper (II) acetate and copper (II) benzoate.

8. The method according to claim 1 in which the zinc compound is a member selected from the group consisting of metallic zinc powder, zinc oxide, zinc halides, zinc sulfate, zinc nitrate, zinc acetate and zinc benzoate.

9. The method according to claim 1 in which the zinc compound is a member selected from the group consisting of zinc chloride and zinc acetate.

* * * * *